US006683176B2

United States Patent
Cooper et al.

(10) Patent No.: US 6,683,176 B2
(45) Date of Patent: Jan. 27, 2004

(54) INTERMEDIATES FOR AND SYNTHESIS OF 3-METHYLENE CEPHAMS

(76) Inventors: Robin D. G. Cooper, 6740 Dover Rd., Indianapolis, IN (US) 46220; Anthony G. M. Barrett, 15 Burlington Gardens - Chiswick, London (GB), W4 4LT (*) Notice: Subject to any disclaimer, the term of this patent is extended or adjusted under 35 U.S.C. 154(b) by 0 days.

(21) Appl. No.: 09/958,857

(22) PCT Filed: Feb. 10, 2001

(86) PCT No.: PCT/US01/04410
§ 371 (c)(1),
(2), (4) Date: Dec. 31, 2001

(87) PCT Pub. No.: WO01/60828
PCT Pub. Date: Aug. 23, 2001

(65) Prior Publication Data

US 2003/0036650 A1 Feb. 20, 2003

Related U.S. Application Data

(60) Provisional application No. 60/183,083, filed on Feb. 16, 2000.

(51) Int. Cl.[7] .................. C07D 501/22; C07D 501/08; C07D 205/095
(52) U.S. Cl. ................. 540/215; 540/222; 540/226; 540/228; 540/229; 540/230; 540/359
(58) Field of Search .................. 540/215, 228, 540/230, 222, 226, 229

(56) References Cited

U.S. PATENT DOCUMENTS 4,052,387 A   10/1977   Kukolja 5,250,525 A   10/1993   Kovacevic et al.

OTHER PUBLICATIONS

J. Org. Chem. 1999, 64, 2190–2913 Waller et. al. Tris(trifluoromethanesulfonyl)methide("Triflide") Anion.

J. Chem. Soc., Perkins I, 1999, 867–871 Barrett et. al. Ytterbium (III) triflate–catalysed preparation of Calix[4] resorcinarenes.

J. Chem. Soc., Perkins I, 1999, 873–878 Walker et. al Lanthanide(III) and Group IV metal triflate catalysed electrophilic nitration.

*Primary Examiner*—Mark L. Berch
(74) *Attorney, Agent, or Firm*—Jeffrey J. Skelton

(57) ABSTRACT

The present invention relates to novel processes for the preparation of 3-methylenecephams. More specifically, the present invention relates to the intramolecular cyclization of penicillin sulfoxide derived monocyclic azetidinone derivatives with organometallic catalysts of the formula III.

$$ME_x(H_2O)_y \qquad \text{(III)}$$

wherein:

M is Sc, Y, La, Ce, Pr, Nd, Sm, Eu, Gd, Tb, Dy, Ho, Er, Tm, Yb, Lu, Zr, Hf, Th, Nb, Ta, U, Bi, or In;

E is $O[SO_2(C_1-C_6 \text{ polyfluoroalkyl})]$, $N[SO_2(C_1-C_6 \text{ polyfluoroalkyl})]_2$, or $C[SO_2(C_1-C_6 \text{ polyfluoroalkyl})]_3$;

x is 3;

y is 0, 1, 2, 3, 4, 5, 6, 7, 8, or 9.

20 Claims, No Drawings

INTERMEDIATES FOR AND SYNTHESIS OF 3-METHYLENE CEPHAMS

This application claims the benefit of U.S. Provisional Application Ser. No. 60/183,083 filed Feb. 16, 2000 and is the national phase of International Application PCT/US01/04410, filed Feb. 10, 2001.

BACKGROUND OF THE INVENTION

Since the early 1940's penicillins, and more recently cephalosporins, have been utilized in man's fight against bacterial infections. These two classes of molecules were the first effective treatments for life threatening infections. Over the past 50 years a tremendous effort has been expended by the scientific community to develop increasingly effective forms of these antibiotics. This effort has led to the identification of specific molecules of great importance to the global medical community. Cefaclor and cephalexin are two examples of cephalosporin antibiotics that have been developed through this process. Despite years of continuing research on new antibiotics, many penicillins and cephalosporins are still widely utilized in the every day fight against pathogenic bacteria.

The primary drawbacks associated with cephalosporins relate to the difficulty and expense of their synthetic production. Several of these important compounds are derived through the synthetic transformation of a penicillin substrate which is itself acquired through a fermentation process. Many steps in the conversion of penicillins to cephalosporins are typically performed using reagents which pose a number of health and environmental risks. In addition, these reagents present economic disadvantages of high outright cost as well as a high cost associated with disposal of the generated waste. These factors significantly affect the overall cost of producing cephalosporin antibiotics.

The present invention relates to novel processes for the preparation of 3-methylenecephams. The present invention utilizes specific catalysts and novel intermediates which have a member of advantages over the analogous procedures known in the art. These catalysts are typically utilized in a less than stoichiometric amount, which may also be recovered and reused, thereby allowing for lower material costs as well as significantly lower waste disposal costs. These two important features combine to lower the overall production cost of 3-methylenecephams and some novel starting materials even eliminate the need for catalysts at all. More specifically, the present invention relates in part to the intramolecular cyclization of penicillin sulfoxide derived monocyclic azetidinone derivatives either thermally or with metal salt catalysts.

SUMMARY OF THE INVENTION

The present invention is directed to a process of preparing compounds of the formula I:

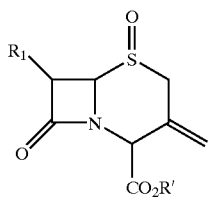

(I)

said process comprising the step of reacting a compound of the formula II;

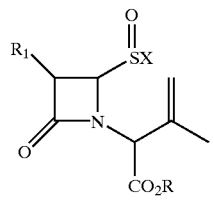

(II)

with a catalyst of the formula III in an inert solvent;

wherein:

M is Sc, Y, La, Ce, Pr, Nd, Sm, Eu, Gd, Tb, Dy, Ho, Er, Tm, Yb, Lu, Zr, Hf, Th, Nb, Ta, U, Bi, or In;

E is $O[SO_2(C_1-C_6 \text{ polyfluoroalkyl})]$, $N[SO_2(C_1-C_6 \text{ polyfluoroalkyl})]_2$, or $C[SO_2(C_1-C_6 \text{ polyfluoroalkyl})]_3$;

x is the common oxidation state of the metal M;

y is 0, 1, 2, 3, 4, 5, 6, 7, 8, or 9;

R is a carboxylic acid protecting group;

R' is hydrogen or a carboxylic acid protecting group;

$R_1$ is a group of the formula;

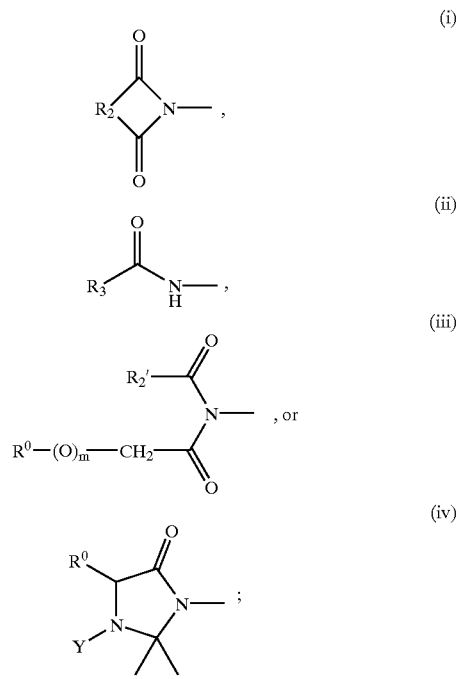

$R_2$ is $C_2-C_4$ alkenylene, $C_2-C_4$ alkylene, 1,2-phenylene, or 1,2-cyclohexenylene;

$R_2'$ is $C_1-C_3$ alkyl, $C_1-C_6$ haloalkyl, $C_1-C_3$ alkoxy, or 2,2,2-trichloroethoxy;

$R_3$ is hydrogen, $C_1-C_3$ alkyl, halomethyl, cyanomethyl, 3-(2-chlorophenyl)-5-methylisoxazol-4-yl, benzyloxy, 4-nitrobenzyloxy, 2,2,2-trichloroethoxy, tert-butoxy, 4-methoxybenzyloxy, phenyl, substituted phenyl, a group of the formula $R^0—(Q)_m—CH_2—$, a heteroarylmethyl group of the formula $R''CH_2—$, or a substituted arylalkyl group of the formula

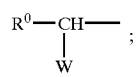

$R^0$ is phenyl, substituted phenyl, 2-thienyl, 3-thienyl, or 1,4-cyclohexyldienyl;

R" is 2-furyl, 3-furyl, 2-thiazolyl, or 5-isoxazolyl;

m is 0 or 1,

Q is O or S;

W is protected hydroxy, or protected amino;

Y is hydrogen, acetyl, or nitroso;

X is chloro, bromo, $-OR_4$, $-SR_5$, or $-NR_6R_7$ wherein: (a) $R_6$ is hydrogen and $R_7$ is hydrogen, phenyl, substituted phenyl, or $-NHR_8$; or wherein (b) $R_6$ is $-COOR_9$ or $-COR_9$ and $R_7$ is $-NH-COOR_9$ or $-NH-COR_9$; or wherein (c) $R_6$, $R_7$, and the nitrogen to which each is attached combine to form an imido group of the formula

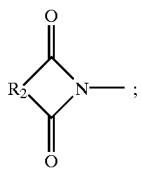

$R_4$ is hydrogen, $C_1-C_{10}$ alkyl, ($C_1-C_3$ alkyl)aryl, $C_1-C_6$ haloalkyl, or $-COR_{10}$;

$R_5$ is $C_1-C_6$ alkyl, phenyl, substituted phenyl, ($C_1-C_3$ alkyl)phenyl, or ($C_1-C_3$ alkyl)substituted phenyl;

$R_8$ is aminocarbonyl, $C_1-C_3$ alkylaminocarbonyl, $C_1-C_3$ alkoxycarbonyl, $C_1-C_3$ alkylcarbonyl, or tosyl;

$R_9$ is $C_1-C_6$ alkyl, or phenyl;

$R_{10}$ is $C_1-C_6$ alkyl, $C_1-C_6$ polyfluoroalkyl, $C_3-C_6$ cycloalkyl, adamantyl, phenyl, substituted phenyl, ($C_1-C_3$ alkyl)phenyl, or ($C_1-C_3$ alkyl)substituted phenyl, or a group of the formula

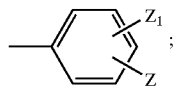

Z is solid polymer support; and $Z_1$ is one or two groups independently selected from the group consisting of hydrogen, halo, hydroxy, protected hydroxy, nitro, cyano, trifluoromethyl, $C_1-C_4$ alkyl, and $C_1-C_4$ alkoxy.

The present invention is also directed towards the novel compounds of Formula IIA below:

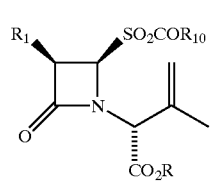

R is a carboxylic acid protecting group;

$R_1$ is a group of the formula;

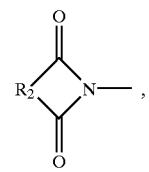

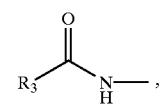

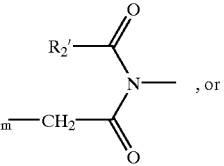

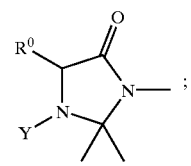

$R_2$ is $C_2-C_4$ alkenylene, $C_2-C_4$ alkylene, 1,2-phenylene, or 1,2-cyclohexenylene;

$R_2'$ is $C_1-C_3$ alkyl, $C_1-C_6$ haloalkyl, $C_1-C_3$ alkoxy, or 2,2,2-trichloroethoxy;

$R_3$ is hydrogen, $C_1-C_3$ alkyl, halomethyl, cyanomethyl, 3-(2-chlorophenyl)-5-methylisoxazol-4-yl, benzyloxy, 4-nitrobenzyloxy, 2,2,2-trichloroethoxy, tert-butoxy, 4-methoxybenzyloxy, phenyl, substituted phenyl, a group of the formula $R^0-(Q)_m-CH_2-$, a heteroarylmethyl group of the formula $R"CH_2-$, or a substituted arylalkyl group of the formula

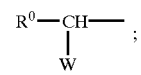

$R^0$ is phenyl, substituted phenyl, 2-thienyl, 3-thienyl, or 1,4-cyclohexyldienyl;

R" is 2-furyl, 3-furyl, 2-thiazolyl, or 5-isoxazolyl;

m is 0 or 1,

Q is O or S;

W is protected hydroxy, or protected amino;

Y is hydrogen, acetyl, or nitroso;

$R_{10}$ is $C_1-C_6$ alkyl, $C_1-C_6$ polyfluoroalkyl, $C_3-C_6$ cycloalkyl, adamantyl, phenyl, substituted phenyl, ($C_1-C_3$ alkyl)phenyl, diphenylmethyl, or ($C_1-C_3$ alkyl) substituted phenyl, or a group of the formula

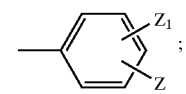

Z is solid polymer support; and $Z_1$ is one or two groups independently selected from the group consisting of hydrogen, halo, hydroxy, protected hydroxy, nitro, cyano, trifluoromethyl, $C_1-C_4$ alkyl, and $C_1-C_4$ alkoxy.

The present invention is also directed towards a process of preparing a compound of Formula I, as described above, wherein said process comprises heating a compound of the Formula IIA, as described above, to a temperature of about 40° C. to about 200° C.

DETAILED DESCRIPTION OF THE INVENTION

The term "$C_1$–$C_{10}$ alkyl" as used herein includes both straight and branched alkyl groups; including but not limited to methyl, ethyl, propyl, butyl, pentyl, hexyl, heptyl, octyl, nonyl, decyl, isopropyl, sec-butyl, tert-butyl, neopentyl, isopentyl, and the like. Included within the definition of "$C_1$–$C_{10}$ alkyl" are also the groups "$C_1$–$C_8$ alkyl", "$C_1$–$C_6$ alkyl", "$C_1$–$C_5$ alkyl", "$C_1$–$C_4$ alkyl", and "$C_1$–$C_3$ alkyl".

The term "alkoxy" as used herein designates an alkyl group attached through an oxygen atom. Examples include but are not intended to be limited to methoxy, ethoxy, pentoxy, and the like.

The term "$C_1$–$C_3$ alkoxycarbonyl" as used herein includes, but is not limited to, methoxycarbonyl, ethoxycarbonyl, propoxycarbonyl, and isopropoxycarbonyl.

The term "$C_1$–$C_6$ polyfluoroalkyl" as used herein includes both straight and branched alkyl groups; including but not limited to methyl, ethyl, propyl, butyl, pentyl, hexyl, which are substituted with from 2–13 fluorine atoms. The number of fluorine atoms will never exceed the available valency of the alkyl group. For example, a methyl group could be substituted with 2 or 3 fluorine atoms, an ethyl group with 2–5 fluorine atoms, and a propyl group with 2–7 fluorine atoms. Substitution can occur independently at any of the available cites.

The term "halo" as used herein includes fluoro, bromo, chloro, and iodo.

The term "protected amino" as employed herein represents amino groups in which the either one or both of the amine hydrogens have been exchanged with a commonly employed protecting group. Protecting groups of this type are well know in the art and are additionally described in: T. W. Greene, *Protective Groups in Organic Synthesis*, John Wiley & sons, (1981) and T. G. Greene and P. Wutz, *Protective Groups in Organic Synthesis, second ed.* Preferred amino protecting groups include but are not limited to tert-butoxycarbonyl, benzyloxycarbonyl, 4-methoxybenzyloxycarbonyl, 4-nitrobenzyloxycarbonyl, 2,2,2-trichloroethoxycarbonyl, allyloxycarbonyl or the 1-carbomethoxy-2-propenyl group formed with methyl acetoacetate.

The term "protected hydroxy" as used herein refers to the readily cleavable groups formed with a hydroxy group such as formyloxy, chloroacetoxy, benzyloxy, benzhydryloxy, trityloxy, 4-nitrobenzyloxy, trimethylsilyloxy, phenacyloxy, tert-butoxy, methoxymethoxy, tetrahydropyranyloxy, and the like. Other hydroxy protecting groups are well know in the art and are additionally described in Greene.

The term "carboxylic acid protecting group" as used herein refers to the commonly used groups employed to block or protect the carboxylic acid functionality while reactions involving other functional sites are carried out. Such groups are well know in the art and are additionally described in Greene. They include by way of example but are not intended to be limited to the following: methyl, tert-butyl, benzyl, 4-methoxybenzyl, allyl, $C_2$–$C_6$ alkanoyloxymethyl, 2-iodoethyl, 4-nitrobenzyl, diphenylmethyl (benzhydryl), phenacyl, 4-halophenacyl, dimethylallyl, 2,2,2-trichloroethyl, and the like. Carboxylic acid protecting group strategies have been utilized with penicillins and cephalosporins for over 50 years and it is important to note that a skilled artisan in the art would appreciate which protecting groups are commonly utilized in this well known area of chemistry.

The term 'substituted as used herein refers to a group which is substituted with 1 or 2 substituents dependently selected from the group consisting of halo, hydroxy, protected hydroxy, nitro, cyano, trifluoromethyl, $C_1$–$C_4$ alkyl, $C_1$–$C_4$ alkoxy, amino, or protected amino. Examples of substituted phenyl include but are not intended to be limited to the following: 4-chlorophenyl, 2,6-dichlorophenyl, 2,5-dichlorophenyl, 3,4-dichlorophenyl, 3-chlorophenyl, 4-bromophenyl, 3,4-dibromophenyl, 3-chloro-4-fluorophenyl, and the like. A protected hydroxyphenyl would include by way of example but is not limited to 4-tetrahydropyranyloxyphenyl, 4-(4-nitrobenzyloxy) phenyl, 2-phenacyloxyphenyl, 4-benzyloxyphenyl, 3-benzyloxyphenyl, 4-tert-butoxyphenyl, 4-benzhydroxyphenyl, 4-trityloxyphenyl, 4-tert-butyldimethylsilyloxyphenyl, and the like. Nitrophenyl groups are 2-nitrophenyl, 3-nitrophenyl, and 4-nitrophenyl. By way of example other substituted groups would include benzyl, aryl, and the like. Importantly, the substituents can be independently selected so that groups like 4-bromo-3-methoxyphenyl, 4-trityloxy-2-nitrophenyl, and the like are included herein.

The term "($C_1$–$C_3$ alkyl) phenyl" as used herein refers to $C_1$–$C_3$ alkyl group substituted with a phenyl group. Likewise any group in "( )" links the functional groups immediately proceeding and following that group.

In the forgoing definitions, hydroxy, amino, and carboxy protecting groups are not exhaustively defined. The function of such groups is to protect the reactive functional groups during the course of the reaction sequence and then be removed at some later time without disrupting the remainder of the molecule. A skilled artisan would appreciate that a wide variety of protection strategies would be applicable to the present invention many of which are well know in the art and have been extensively studied and published.

Imido groups represented when $R_2$ is $C_2$–$C_4$ alkenylene are maleimido, 3-ethylmaleimido, 3,4-dimethylmaleimido, and like imido groups. Imido groups represented when R is 1,2-cyclohexenylene or 1,2-phenylene are 3,4,5,6-tetrahydrophthalimido or phthalimido (Ft) respectively.

Preferred Embodiments

Preferred compounds of the formula II or IIA for use in present invention include compounds wherein:

R is
a) a penicillin or cephalosporin carboxylic acid protecting group,
b) p-nitrobenzyl,
c) p-methoxybenzyl,
d) $C_1$–$C_6$ alkyl,
e) substituted $C_1$–$C_6$ alkyl,
f) phenyl,
g) substituted phenyl,
h) diphenylmethyl,
i) trichloroethyl,
j) benzyl, or
k) substituted benzyl.

$R_1$ is
a) a penicillin or cephalosporin amino side chain,
b) PhOCH$_2$CONH—(V—), PhCH$_2$CONH— (G—), or phthalimido (Ft-)

c) phthalimido.

$R_{10}$ is a) $C_1$–$C_6$ alkyl, b) methyl, c) t-butyl, d) substituted $C_1$–$C_6$ alkyl, e) phenyl, f) substituted phenyl, g) dimethylphenyl h) benzyl, i) substituted benzyl j) phenyl bonded to a polymer support.

X is a) chloro b) $OR_4$ c) bromo

Halo is preferably chloro or bromo.

Synthetic Methodology

The penicillin sulfoxide ester precursors to the compounds of formula II are either know, readily available, or described herein; many of which have been utilized in the art for the preparation of cepham compounds. By way of example, they can be prepared from 6-acylamino and 6-imidopenicillin acids by a) esterification and b) subsequent oxidation, usually with MCPBA, peracetic acid, or sodium periodate.

The starting materials used to prepare compounds of formula II are well known in the art and readily prepared by known processes. See for example, S. Kukolja and S. R. Lammert, *Angew. Chem.*, 12, 67–68 (1973); Kukolja U.S. Pat. No. 4,052,387; and Kukolja U.S. Pat. No. 4,159,266 all herein incorporated by reference.

Catalyzed Cyclization

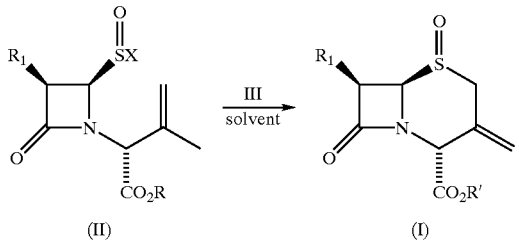

It has been recognized in the art that other derivatives of azetidinone sulfinyl chlorides can be prepared by known methods, including sulfite esters, thiosulfinate esters, and sulfinamides, and sulfinimides. Such derivatives can be prepared by well-known conventional procedures for making the analogous carboxylic acid derivatives. In addition to cyclizing the sulfinyl chlorides directly, the cyclization methodology of the present invention is applicable and can be directed to such compounds.

The cyclization reaction of the present invention can be catalyzed by a catalyst of the formula III;

$$ME_x(H_2O)_y \quad (III)$$

wherein M is selected from the group consisting of Sc, Yb, La, Ce, Pr, Nd, Sm, Eu, Gd, Tb, Dy, Ho, Er, Tm, Yb, Lu, Zr, Hf, Th, Nb, Ta, U, Bi, or In. E is $O[SO_2(C_1$–$C_6$ polyfluoroalkyl)]$, $N[SO_2(C_1$–$C_6$ polyfluoroalkyl)]_2$, or $C[SO_2(C_1$–$C_6$ polyfluoroalkyl)]_3$; x is the common oxidation state of the metal M; and y is 0, 1, 2, 3, 4, 5, 6, 7, 8, or 9. A skilled artisan would appreciate that the lanthanides would be applicable to the present invention. Preferred metals (M) include Hf, Sc, Zr, Bi, and Yb; the most preferred is Yb. E is preferably $O(SO_2CF_3)$. E is also preferably $N(SO_2CF_3)_2$. Preferably x is 3, and y is 0 or 3 The molecules of water associated with the catalyst will vary depending on the particular metal (M) utilized and its oxidation state. The catalyst's level of hydration may or may not be crucial depending on the circumstance of the reaction and is typically determined by the stability of the particular complex and is primarily based on convenience and availability. The level of hydration is typically from 0–4 moles per mole of catalyst.

The temperature at which the cyclization of the present invention is performed is not crucial and can vary depending on the reactivity of both the catalyst and the particular compound of formula II which is being cyclized. The process is most preferably performed at room temperature. Alternatively, a temperature range from about 10° C. to about 50° C. is preferred. Alternatively, the process can be performed at the reflux temperature of the solvent medium, which would typically range from about 50° C. to about 200° C. Most preferably a reflux temperature would be from about 70° C. to about 120° C. A skilled artisan would appreciate that the exact temperature of the reaction is not crucial as long as the rate of the cyclization is sufficient to provide a reasonable half-life of the starting material and product. Often one may choose a slightly lower reaction temperature, including sub-ambient temperatures, to avoid detrimental side reactions that would lower the overall yield and purity of the product. Given specific compounds of formula II and III temperatures as low as 0° C. may be appropriate.

Similarly, the solvent chosen for the reaction is not crucial. The solvent must be substantially inert to the other reactants and sufficiently effective to dissolve the reactants allowing them to react. The reaction need not, and may preferably not, be homogenous. A wide variety of polar and non-polar solvents may be utilized in the present invention. Choice of appropriate solvent will be determined by the characteristics of the particular compounds of formula II IIA and III, as well as the temperature at which one seeks to run the process. Preferred solvents include nitromethane, acetonitrile, tetrahydrofuran, ethers, alkanes, and mixtures thereof. Most preferred solvents include nitromethane, and acetonitrile, and mixtures thereof. Most preferred compounds of Formula II are those wherein X is chloro.

Preparation of Compounds of Formula IIA

The compounds of Formula IIA can be prepared by techniques known in the art and according to the following scheme.

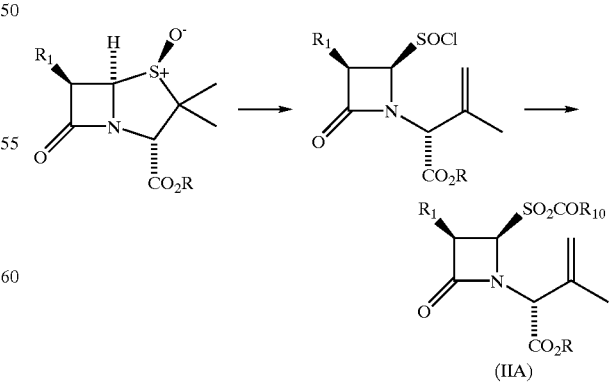

Protected penicillin sulphoxide is converted to the corresponding protected sulphinyl chloride by procedures well know in the art (see Kukolja supra). The reaction is preferably performed utilizing N-chlorosuccinamide or N-chlorophthalimide in e.g. toluene, dichloroethane or carbon tetrachloride at reflux from about 20 minutes to 1 hour. The chloride can then be displaced by the metal salt of a carboxylic acid to form the compounds of formula IIA, wherein $R_{10}$ is preferably derived from a hindered carboxylate salt. Preferred salts include sodium, potassium, and silver but a skilled artisan would appreciate that a wide variety of salts would function in this transformation. In addition, a wide variety of carboxylic acids would react to provide compounds of Formula IIA. Most preferably the salts are purified and dried shortly before use, or may be alternatively be fused before use and the reaction performed with sonication. The reaction time is typically from about 1–48 hours, most preferably about 24 hours. The reaction is typically performed at room temperature but may be performed a temperatures ranging from −78° C. to the reflux temperature of the solvent. As stated above, the choice of solvent is not critical and may be determined by cost or convenience. Preferred solvents include toluene and THF and preferably the reaction solvent is approximately a 2:1–1:1 mixture of toluene and THF. In addition, the reaction is preferably performed in the dark with dry solvents to minimize undesired side reactions.

Thermal Cyclization

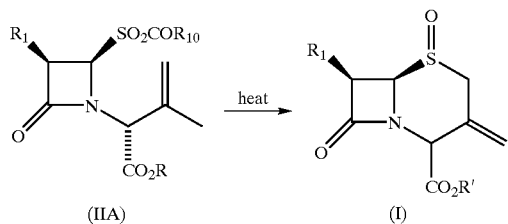

The inventors have surprisingly discovered that compounds of Formula IIA cyclize to compounds of Formula I under thermal conditions. This type of thermal cyclization is unprecedented in the literature and has tremendous advantages over methods currently practiced in the art which require expensive catalysts that are cumbersome to utilize and a problem to dispose of safely.

The thermal cyclization occurs by heating a compound of Formula IIA to a temperature of from about 40° C. to about 200° C. The reaction can be performed neat or in the presence of a solvent. The reaction is preferably performed neat under vacuum. Conducting the reaction under vacuum has the advantage that the succinimide produced in the synthesis the compounds of Formula IIA sublimes from the reaction mixture. The preferred reaction temperature is about 55° C. The preferred reaction time is from about 0.5 hours to about 24 hours. The skilled artisan will appreciate that the rate of the reaction and production of side products will vary depending on the temperature and duration of the reaction. Preferred temperatures and duration of reaction will vary depending on the particular substrate of Formula IIA.

Transformation to Cephalosporin Antibiotics

The product 3-methylenecephems sulfoxides of the process of this invention are useful intermediates in the preparation of cephalosporin antibiotics.

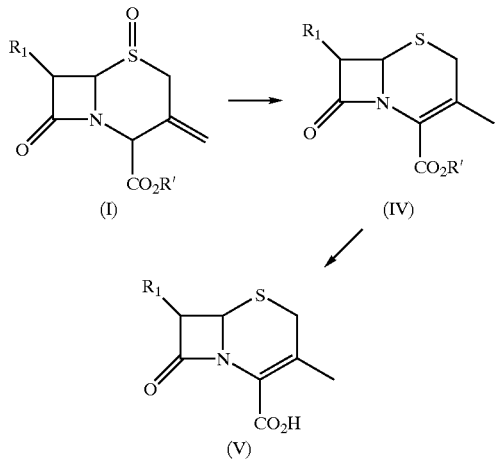

The sulfoxides of Formula I can be reduced by known procedures, typically with phosphorous trichloride or phosphorous tribromide in dimethylformamide, to provide the corresponding 3-methylenecephems which are predictably converted to desacetoxycephalosporins of Formula IV, upon treatment with triethylamine in dimethylacetamide. [Chauvette and Pennington, J. Org. Chem., 38, 2994 (1973)]. The desacetoxycephalosporin esters are converted to active antibiotics of Formula V, by cleaving the ester function. Deprotection of the acid functionality is well known in the art and the procedures will vary depending on the specific protecting group.

Alternatively the exomethylenecephams can be employed in the preparation of other cephem antibiotics of the formula VI;

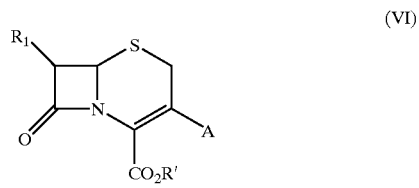

Wherein A may be but is not limited to chloro, bromo, methoxy, triflyl, triflyloxy, mesyl, tosyl, hydrogen, thioether, alkyl, alkenyl, or aryl.

Such chemical conversions, as well as too many others to mention, have been disclosed in the art and are well known. [see e.g. Chauvette and Pennington, JACS., 96, 4986 (1974).] For a review of 3-chlorocephem and other 3 derivatives see, The Chemistry and Biology of Betalactam Antibiotics, vol. 1, edited by, Morin and Gorman, Academic Press, 1982 Chapter 2, p 93. (See also; Tetrahedron Letters, 6043, 1988. Heterocycles, 23, 1901, 1985. J. Organic Chemistry, 54, 4962, 1989. J. Organic Chemistry, 54, 5828, 1989. Tetrahedron Letters, 3389, 1990. Synthetic Communications 20, 2185, 1990. Tetrahedron Letters, 4073, 1991. J. Organic Chemistry, 58, 2296, 1993. Tetrahedron Letters. 7229, 1993. J. Antibiotics, 47, 453, 1994. J. Antibiotics, 44, 498, 1991. Helv Chim Acta, 60, 1510, 1977.)

In general, the exomethylenecephem compounds maybe converted by low temperature ozonolysis, to 3-hydroxycephems or the 3-keto equivalents which are in turn treated with diazomethane at room temperature to afford the 3-methoxycephem derivatives. The 3-halocephems are derived from the 3-hydroxycephem esters by treatment with a halogenating agent such as thionyl chloride, phosphorous trichloride, or phosphorous tribromide by methods known in the art. The corresponding deprotected cephem acids exhibit antibacterial activity. The 3-hydroxy group can also be converted into the triflyloxy compound which can then be converted into many different 3-carbon substituted cephems or many different thio substituted cephems.

PREPARATIONS AND EXAMPLES

The following Examples are intended to demonstrate the effectiveness of the present invention. They are not intended to specifically define the variety of conditions under which the present invention can be performed or limit the scope of the claims in any way. A skilled artisan will appreciate, and Applicants assert, that numerous individual alterations of the conditions described herein will also yield effective results.

General:

All reactions were conducted, but need not be, under a dry inert atmosphere (argon or nitrogen). All glassware was dried before use in an oven (ca. 150° C.) or flame dried under argon and cooled under a dry inert atmosphere. Solvents and reagents were purified and dried as described by Perrin and Armarego; $CCl_4$ was distilled from $P_2O_5$ and stored over 4 Å molecular sieves under a dry inert atmosphere. (3R, 5R, 6R)-Methyl 6-phthalimidopenicillanate sulphoxide was dried over $P_2O_5$ in vacuo for 48 h and then stored in a desiccator containing self indicating silica gel. (2R)-Methyl 2-[(2R, 3R)-2-acetoxysulphinyl-4-oxo-3-phthalimido-1-azetidinyl]-3-methyl-3-butenoate was stored temporarily in a desiccator containing self indicating silica gel. N-Chlorosuccinimide was crystallised from AcOH, washed with AcOH then hexane and dried in vacuo for 48 h and stored at 4° C. in the dark. NaOAc is hygroscopic and was used directly from a fresh bottle, or was fused in situ under vacuum (ca. 0.1 mmHg). ESI mass spectra were recorded in the positive ion mode.

For determination of the yields in the conversion of (2R)-methyl 2-[(2R, 3R)-2-acetoxysulphinyl-4-oxo-3-phthalimido-1-azetidinyl]-3-methyl-3-butenoate to methyl 3-methylene-7-phthalimidocepham-4-carboxylate 1-oxide the internal standard method was used. A reference mixture of methyl 3-methylene-7-phthalimidocephamrcarboxylate 1-oxide and the internal standard tri-tert-butylbenzene was prepared for calibration. The internal standard produced a peak with an disproportionately greater area than that for the azetidinone peaks. After drying the product mixtures in vacuo, 1 equivalent of tri-tert-butylbenzene was added. The mixtures were then dissolved in $CDCl_3$ and analyzed by $^1H$ NMR spectroscopy. The integral was measured from 1.2 to 1.5 ppm for the trimethyl signal (1.34 in $CDCl_3$) of the internal standard and was compared to those of both azetidinone signals (5.95 and 4.90) summed together for the (R)-diastereoisomer of methyl 3-methylene-7-phthalimidocepham-4-carboxylate 1-oxide. In mixtures where the (S)-diastereoisomer of methyl 3-methylene-7-phthalimidocepham-4-carboxylate 1-oxide was visible these peaks were also measure (5.62 and 4.91).

Example 1

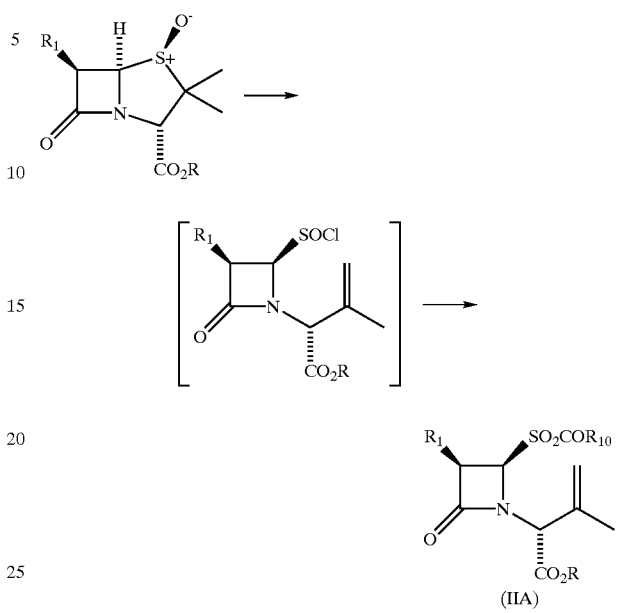

(2R)-Methyl 2-[(2R, 3R)-2-acetoxysulphinyl-4-oxo-3-phthalimido-1-azetidinyl]-3-methyl-3-butenoate. ($R_1$=Ft, R=methyl, and $R_{10}$=methyl)

i) Using AgOAc:

A solution of (3R, 5R, 6R)-methyl 6-phthalimidopenicillanate sulphoxide (250 mg, 0.66 mmol) and N-chlorosuccinimide (89 mg, 0.66 mmol) in $CCl_4$ (14 mL) was stirred under reflux under an atmosphere of argon for 70 min. Once the solution had cooled AgOAc (110 mg, 0.66 mmol) was added and the mixture was stirred under reflux for a further 40 min. The product mixture was diluted with $CHCl_3$ (20 mL), the solids allowed to settle and filtered whilst hot using a heated metal cannula fitted with a filter paper filter into another vessel. The remaining silver salts were washed with $CHCl_3$ (10 mL) and the filtration procedure was repeated. The combined $CHCl_3$ portions were washed with distilled water (5 mL) and saturated aqueous solution of NaCl (10 mL), dried ($MgSO_4$) and evaporated to give a white foam (295 mg). It is not necessary to wash the product with water, however, this removes succinimide produced in the reaction. The $^1H$ NMR spectrum of the crude product revealed that it was composed of the title compound (82% of the mixture as a 1:1 mixture of diastereoisomers, epimeric at sulphur), (2R)-methyl 2-[(2R, 3R)-2-chloro-4-oxo-3-phthalimido-1-azetidinyl]-3-methyl-3-butenoate (4% of the mixture), (2R)-methyl 2-[(2R, 3S)-2-acetoxy-4-oxo-3-phthalimido-1-azetidinyl]-3-methyl-3-butenoate (3% of the mixture), methyl 3-methylene-7-phthalimidocepham-4-carboxylate-1-oxide (10% of the mixture) and putative (2R)-methyl 3-methyl-2-[(2R, 3S)-2-succinimidyl-4-oxo-3-phthalimido-1-azetidinyl]-3-butenoate (0.6% of the mixture). Only the NMR signals for the title compound are reported $^1H$ NMR ($CDCl_3$, 300 MHz) 1.91 (s, 3H, OAc), 2.00 (s, 3H, $CH_3$), 2.03 (s, 3H, $CH_3$), 2.12 (s, 3H, OAc), 383 (s, 3H, $CO_2C\underline{H}_3$), 3.85 (s, 3H, $CO_2CH_3$), 4.98 (s, 1H), 5.07 (s, 1H), 5.08 (s, 1H), 5.18 (s, 1H), 5.24 (d, J=1.3 Hz, 1H), 5.39 (d, J=5.3 Hz, 1H, azetidinyl-H), 5.42 (s, J=5.0 Hz, 1H, azetidinyl-H), 5.76 (d, J=5.0 Hz, 1H, azetidinyl-H), 5.83 (d, J=5.3 Hz, 1H, azetidinyl-H), 7.78 (m, phthalimido), 7.88 (m, phthalimido); $^{13}$C NMR (CDCl$_3$) 20.3, 20.8, 21.0, 21.1, 52.6, 52.7, 55.8, 56.5, 58.9, 60.5, 75.3, 79.2, 116.9, 118.7, 123.9, 131.0, 131.5, 134.6, 135.0, 137.3, 138.9, 163.6, 163.8, 166.3, 166.5, 167.5, 167.8, 168.5, 168.6; CIMS m/z 394 [93%, (M-58)NH4], 377 [34, (M-58)H+], 376 (94, M-58), 359 (48), 346 (51), 329 (35), 297 (21), 190 (20), 189 (20), 172 (30), 130 (100), 124 (47), 112 (91), 80 (15), 59 (24); ESIMS (MeCN) m/z 473 (40%, MK+), 457 (100, MNa+), 435 (60, MH+); ESIMS (MeCN, CsI) 567 (100%, MCs+); IR (thin film, KBr) 1792 (m), 1778 (m), 1725 (s), 1387 (m), 1190 (w), 1164 (w), 1138 (w), 718 (w).

ii) Using NaOAc:

A solution of (3R, 5R, 6R)-methyl 6-phthalimidopenicillanate sulphoxide (25 mg, 0.07 mmol) and N-chlorosuccinimide (9 mg, 0.07 mmol) in CCl$_4$ (1.4 mL) was stirred under reflux under an atmosphere of argon for 70 min. To the product was added NaOAc (6 mg, 0.07 mmol) and the heterogeneous mixture was stirred under reflux for 1 h. The mixture was diluted with CHCl$_3$ (3.5 mL), dried (MgSO$_4$), filtered and evaporated to give a transparent oil (32 mg). The $^1$H NMR spectrum of the crude product revealed that it was composed of the title compound (64% of the mixture as a 1:1 mixture of diastereoisomers, epimeric at sulphur), (2R)-methyl 2-[(2R, 3R)-2-chloro-4-oxo-3-phthalimido-1-azetidinyl]-3-methyl-3-butenoate (17% of the mixture), (2R)-methyl 2-[(2R, 3S)-2-acetoxy-4-oxo-3-phthalimido-1-azetidinyl]-3-methyl-3-butenoate (15% of the mixture), putative (2R)-methyl 3-methyl-2-[(2R, 3S)-2-succinimidyl-4-oxo-3-phthalimido-1-azetidinyl]-3-butenoate (4% of the mixture) and succinimide. The succinimide can be removed by an aqueous wash.

The following examples were prepared substantially in accordance with the procedure above with the variations noted below. The products were not isolated but rather were characterized by NMR using known resonances of the azetidinone protons and were reacted directly to prepare compound of Formula I. Ft=phthalimido, PNB=p-nitrobenzyl, V=phenoxyacetyl

| Ex.# | R$_1$ | R | R$_{10}$Salt | Time/T/sol. |
|---|---|---|---|---|
| 1a | Ft | Methyl | AcONa | 1h/reflux/CCl$_4$ |
| 1b | Ft | Methyl | AcOAg | 40 min/reflux/CCl$_4$ |
| 1c | Ft | Methyl | BzOAg | 40 min/reflux/CCl$_4$ |
| 1d | V | PNB | AcOAg | 18h/RT/Tol |
| 1e | V | PNB | AcONa | 18h/RT/Tol-THF |
| 1e | V | PNB | AcOK | 18h/RT/Tol |
| 1f | V | PNB | BzOAg | 15.5h/RT/Tol |
| 1g | V | PNB | BzOK | 21h/RT/Tol-THF |
| 1h | V | PNB | 1-adamantyl—CO$_2$Na | 25h/RT/THF/ |
| 1I | V | PNB | Me$_3$CCO$_2$Na | 18h/RT/Tol-Ether |

Example 2

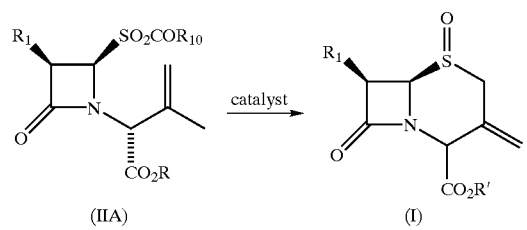

(4R, 6R, 7R)-Methyl 3-methylene-7-phthalimidocepham 4-carboxylate-1-oxide (R$_1$=Ft, R=methyl, and R$_{10}$=methyl)

i) Ytterbium(III) triflate-catalysed cyclization of sulphinyl acetates in MeNO$_2$:

To (2R)-methyl 2-[(2R, 3R)-2-acetoxysulphinyl-4-oxo-3-phthalimido-1-azetidinyl]-3-methyl-3-butenoate (15 mg, ca. 0.035 mmol since not pure) in MeNO$_2$ (500 L) was added [Yb(OH$_2$)$_9$](OTf)$_3$ (2.7 mg, 0.004 mmol). The mixture was stirred at room temperature for 3 (run 1) and 5 h (run 2). The mixtures were diluted with CHCl$_3$ (1.5 mL) and washed with a saturated aqueous solution of NaCl (0.2 mL). The aqueous wash was extracted with CHCl$_3$ (0.5 mL). The combined CHCl$_3$ was dried MgSO$_4$), filtered and evaporated to provide the title product (run 1: 11 mg; run 2: 12 mg). To the dried products was added tri-tert-butylbenzene (8.6 mg in each, 0.035 mmol). The mixtures were dissolved in CDCl$_3$ and analysed by $^1$H NMR spectroscopy. Because one of the (S)-diastereoisomer signals (5.62) was obscured by other resonances and therefore not measurable, the integral totals for the signals at ca. 4.9 [(R)- and (S)-diastereoisomers present as overlapping doublets) were doubled to estimate the total for both diastereoisomers. These values were scaled with reference to the internal standard and divided by the total measured for the (R)-diastereoisomer of title compound in a reference run [13 mg, 0.035 mmol and tri-tert-butylbenzene (8.6 mg, 0.035 mmol) in CD$_3$NO$_2$ (500 L)] indicating yields of 65 (run 1) and 73% (run 2).

ii) Ytterbium(III) triflate-catalysed cyclisation of sulphinyl acetates in MeNO$_2$:

To (2R)-methyl 2-[(2R, 3R)-2-acetoxysulphinyl-4-oxo-3-phthalimido-1-azetidinyl]-3-methyl-3-butenoate (60 mg, ca. 0.14 mmol since not pure) in MeNO$_2$ (2 mL) was added [Yb(OH$_2$)$_9$](OTf)$_3$ (11 mg, 0.014 mmol). The mixture was stirred for 5 h at room temperature and was then diluted with CHCl$_3$ (6 mL) and washed with a saturated aqueous solution of NaCl (0.8 mL). The aqueous portion was extracted twice with CHCl$_3$ (2 mL then 1 mL). The combined CHCl$_3$ was dried MgSO$_4$), filtered and evaporated to provide a yellow gum (56 mg). This was purified by radial chromatography (1 mm plate of SiO$_2$; 10% EtOAc in methylene chloride with a 10% EtOAc gradient per 15 mL) giving two fractions [(R)- then the (S)-diastereoisomer of the title compound, total 27 mg, 0.072 mmol, 51% in a 4.4:1.0 ratio).

The following examples were prepared substantially in accordance with the procedure above with the variations noted below. The yield expressed is either crude or isolated and includes all isomeric forms of the desired product. The products were characterized by NMR using the known resonances of the azetidinone protons. These resonances are well known and very distinctive.

| Ex.# | R$_1$ | R | R$_{10}$ | Time/T/sol. | Catalyst | Yield |
|---|---|---|---|---|---|---|
| 2a | Ft | Methyl | Methyl | 3h/RT/MeNO$_2$ | [Yb(OH$_2$)$_3$](OTf)$_3$ | 65% |
| 2b | Ft | Methyl | Methyl | 5h/RT/MeNO$_2$ | [Yb(OH$_2$)$_3$](OTf)$_3$ | 73% |
| 2c | Ft | Methyl | Methyl | 6d/RT/MeAc | Yb(OTf)$_3$ | 10% |

-continued

| Ex.# | $R_1$ | R | $R_{10}$ | Time/T/sol. | Catalyst | Yield |
|---|---|---|---|---|---|---|
| 2d | Ft | Methyl | Methyl | 7.5h/RT/EtNO$_2$ | [Yb(OH$_2$)$_3$](OTf)$_3$ | 40% |
| 2e | Ft | Methyl | Methyl | 7.5h/RT/AcOR | [Yb(OH$_2$)$_3$](OTf)$_3$ | 20% |
| 2f | Ft | Methyl | Methyl | 68h/RT/MeCN | Yb(OTf)$_3$ | >10% |
| 2g | Ft | Methyl | Methyl | 68h/RT/CH$_2$Cl$_2$ | Yb(OTf)$_3$ | >10% |
| 2h | Ft | Methyl | Methyl | 68h/RT/THF | Yb(OTf)$_3$ | >10% |
| 2I | Ft | Methyl | Phenyl | 3h/RT/MeNO$_2$ | [Yb(OH$_2$)$_3$](OTf)$_3$ | 50% |
| 2j | V | PNB | CMe$_3$ | 23h/RT/MeNO$_2$ | Yb(OTf)$_3$ | 56% |
| 2k | V | PNB | 1-adamantyl | 45h/RT/MeNO$_2$ | Yb(OTf)$_3$ | 24% |

NMR of product from 2j $^1$H NMR(CDCl$_3$, 270 MHz) δ 3.2(1H, d, H2a), 3.62(1H, d, H2b), 4.54(2H, s, PhOCH$_2$), 5.21(1H, s), 5.27(2H, s, CO$_2$CH$_2$), 5.29(1H, s), 5.31(1H, s), 5.43(1H, d,), 5.76(1H, dd,), 7.9(2H, d, Ph), 7.0(1H, t, Ph), 7.32(2H, t, Ph), 7.49(2H, d, ArNO$_2$), 8.25(2H, d, ArNO$_2$).

Example 3

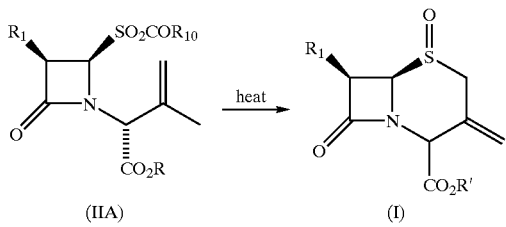

The following examples were prepared as noted below. The yield expressed is either crude or isolated and includes all isomeric forms of the desired product. The products were characterized by NMR using the known resonances of the azetidinone protons and as described in Example 3.

| Ex.# | $R_1$ | R | $R_{10}$ | Time/T/sol. | Yield |
|---|---|---|---|---|---|
| 3a | V | PNB | Methyl | 4h/reflux/Tol | 26% |
| 3b | V | PNB | Methyl | 0.5h/125°/neat | 28% |
| 3c | V | PNB | Methyl | 13h/55°/neat | 50% |
| 3d | V | PNB | Phenyl | 0.5h/125°/neat | 22% |
| 3e | V | PNB | CMe$_3$ | 1h/100°/neat | 18% |
| 3f | V | PNB | CMe$_3$ | 4.5h/reflux/Tol | 17% |
| 3g | V | PNB | CMe$_3$ | 19h/65°/neat | 29% |
| 3h | V | PNB | Benzyl | .5h/125°/neat | 31% |

Example 4

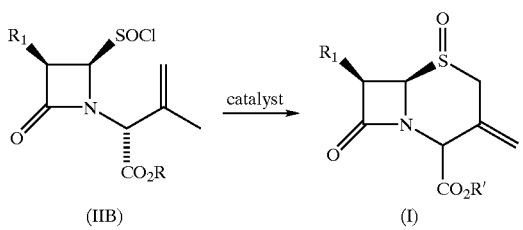

The following sulphinyl chloride derivative of Formula IIB was reacted under conditions illustrated below and as described in Example 2, to provide products of Formula I.

| Ex.# | $R_1$ | R | Catalyst | Time/T/sol. | Yield |
|---|---|---|---|---|---|
| 4a | V | PNB | Yb(OTf)$_3$ | 40h/rt/MeNO$_2$[1] | 53% |
| 4b | V | PNB | Yb(OTf)$_3$ | 38h/rt/MeNO$_2$[1] | 64%[2] |
| 4c | V | PNB | [Yb(OH$_2$)$_3$](OTf)$_3$ | 120h/rt/MeNO$_2$[1] | 12%[2] |
| 4d | V | PNB | Yb(OTf)$_3$ | 21h/rt/MeNO$_2$ | 46%[2] |
| 4e | V | PNB | Yb(OTf)$_3$ | 22h/rt/MeNO$_2$ | 30%[2] |
| 4f | V | PNB | Yb(OTf)$_3$ | 22h/rt/MeNO$_2$ | 72%[2] |
| 4g | V | PNB | Yb(OTf)$_3$ | 22h/rt/MeNO$_2$ | 57%[2] |

[1] 1 eq. Sodium t-butyl acetate added
[2] Yield determined by NMR and as described in Example 2.

We claim:

1. A process of preparing compounds of the formula I:

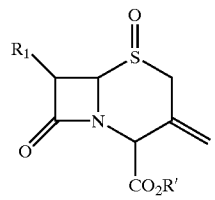

(I)

said process comprising the step of reacting a compound of the formula II;

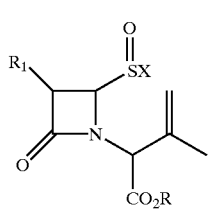

(II)

$$ME_x(H_2O)_y \quad (III)$$

with a catalyst of the formula III in an inert solvent; wherein:

M is Sc, Y, La, Ce, Pr, Nd, Sm, Eu, Gd, Tb, Dy, Ho, Er, Tm, Yb, Lu, Zr, Hf, Th, Nb, Ta, U, Bi, or In;

E is O[SO$_2$(C$_1$–C$_6$ polyfluoroalkyl)], N[SO$_2$(C$_1$–C$_6$ polyfluoroalkyl)]$_2$, or C[SO$_2$(C$_1$–C$_6$ polyfluoroalkyl)]$_3$;

x is 3 or when M is Th then x is 4;

y is 0, 1, 2, 3, 4, 5, 6, 7, 8, or 9;

R is a carboxylic acid protecting group;

R' is hydrogen or a carboxylic acid protecting group;

$R_1$ is a group of the formula;

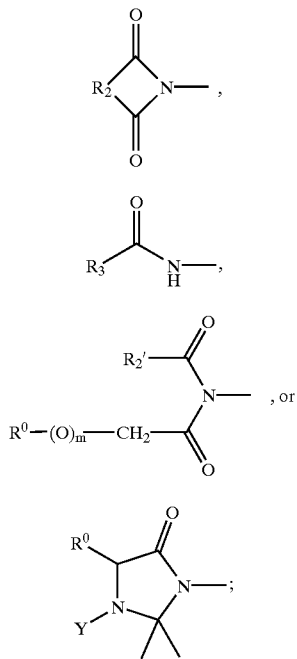

$R_2$ is $C_2$–$C_4$ alkenylene, $C_2$–$C_4$ alkylene, 1,2-phenylene, or 1,2-cyclohexenylene;

$R_2'$ is $C_1$–$C_3$ alkyl, $C_1$–$C_6$ haloalkyl, $C_1$–$C_3$ alkoxy, or 2,2,2-trichloroethoxy;

$R_3$ is hydrogen, $C_1$–$C_3$ alkyl, halomethyl, cyanomethyl, 3-(2-chlorophenyl)-5-methylisoxazol-4-yl, benzyloxy, 4-nitrobenzyloxy, 2,2,2-trichloroethoxy, tert-butoxy, 4-methoxybenzyloxy, phenyl, substituted phenyl, a group of the formula $R^0$—$(Q)_m$—$CH_2$—, a heteroarylmethyl group of the formula $R''CH_2$—, or a group of the formula

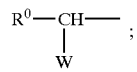

$R^0$ is phenyl, substituted phenyl, 2-thienyl, 3-thienyl, or 1,4-cyclohexyldienyl;

R" is 2-furyl, 3-furyl, 2-thiazolyl, or 5-isoxazolyl;

m is 0 or 1,

Q is O or S;

W is protected hydroxy, or protected amino;

Y is hydrogen, acetyl, or nitroso;

X is chloro, bromo, —$OR_4$, —$SR_5$, or —$NR_6R_7$ wherein:
(a) $R_6$ is hydrogen and $R_7$ is hydrogen, phenyl, substituted phenyl, or —$NHR_8$; or wherein (b) $R_6$ is —$COOR_9$ or —$COR_9$ and $R_7$ is —NH—$COOR_9$ or —NH—$COR_9$; or wherein (c) $R_6$, $R_7$, and the nitrogen to which each is attached combine to form an imido group of the formula

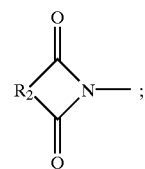

$R_4$ is hydrogen, $C_1$–$C_{10}$ alkyl, ($C_1$–$C_3$ alkyl)aryl, $C_1$–$C_6$ haloalkyl, or —$COR_{10}$;

$R_5$ is $C_1$–$C_6$ alkyl, phenyl, substituted phenyl, phenyl ($C_1$–$C_3$ alkyl), or substituted phenyl($C_1$–$C_3$ alkyl);

$R_8$ is aminocarbonyl, $C_1$–$C_3$ alkylaminocarbonyl, $C_1$–$C_3$ alkoxycarbonyl, $C_1$–$C_3$ alkylcarbonyl, or tosyl;

$R_9$ is $C_1$–$C_6$ alkyl, or phenyl;

$R_{10}$ is $C_1$–$C_6$ alkyl, $C_1$–$C_6$ polyfluoroalkyl, $C_3$–$C_6$ cycloalkyl, adamantyl, phenyl, substituted phenyl, ($C_1$–$C_3$ alkyl)phenyl, or substituted phenyl($C_1$–$C_3$ alkyl), or a group of the formula

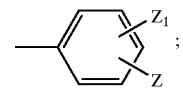

Z is solid polymer support; and $Z_1$ is one or two groups independently selected from the group consisting of hydrogen, halo, hydroxy, protected hydroxy, nitro, cyano, trifluoromethyl, $C_1$–$C_4$ alkyl, and $C_1$–$C_4$ alkoxy.

2. The process of claim 1 wherein: X is chloro, bromo, or $OR_4$.

3. The process of claim 2 wherein: X is $OR_4$ and $R_4$ is methyl, benzyl, or t-butyl.

4. The process of claim 1 wherein:

$R_1$ is a group of the formula

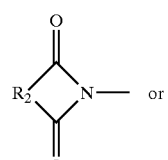

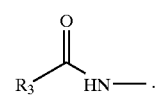

5. The process of claim 1 wherein:

$R_1$ is a group of the formula

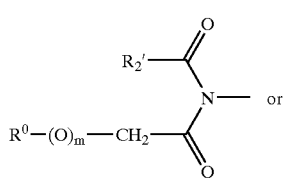

(iv) 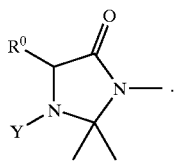

6. The process of claim 4 wherein:
$R_1$ is a phthalimido, phenoxyacctylamino, or phenylacctylamino.

7. The process of claim 6 wherein: $R_1$ is a phthalimido.

8. The process of claim 6 wherein:
R is $C_1$–$C_6$ alkyl, phenyl, benzyl, p-nitrobenzyl, p-methoxybenzyl, diphenylmethyl, or trichloroethyl.

9. The process of claim 8 wherein:
R is methyl, p-nitrobenzyl, diphenylmethyl, or trichloroethyl.

10. The process of claim 4 wherein:
R is methyl, p-nitrobenzyl, diphenylmethyl, or trichloroethyl; and
X is chloro, bromo, or $OR_4$.

11. The process of claim 10 wherein:
$R_1$ is phenoxyacetylamino; R is p-nitrobenzyl; and X is chloro.

12. The process of claim 1 wherein the reaction temperature is from about 20° C. to about 70° C.

13. The process of claim 10 wherein the reaction temperature is from about 20° C. to about 70° C.

14. The process of claim 10 wherein the reaction solvent is nitromethane, acetonitrile, or a mixture thereof.

15. The process of claim 1 wherein M is Hf, or Yb.

16. The process of claim 10 wherein M is Hf or Yb; and is $O(SO_2CF_3)$.

17. The process of claim 1 wherein M is Yb, E is $O(SO_2CF_3)$, and y is 0 or 3.

18. The process of claim 10 wherein M is Yb, E is $O(SO_2CF_3)$, and y is 0 or 3.

19. The process of claim 1 further comprising the step of converting a compound of Formula I to a compound of Formula (VI)

(VI) 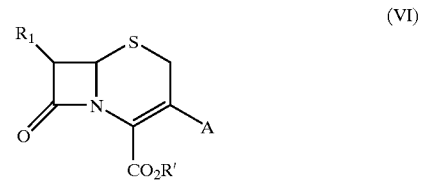

wherein A is chloro, bromo, hydroxy, methoxy, triflyl, mesyl, tosyl, hydrogen, $C_1$–$C_4$ alkyl, or $C_1$–$C_4$ alkenyl.

20. The process of claim 10 further comprising the step of converting a compound of Formula I to a compound of Formula (VI)

(VI) 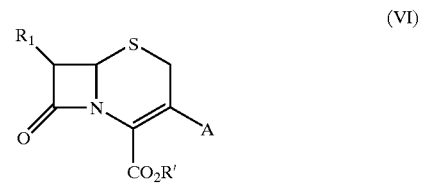

wherein A is chloro, bromo, hydroxy, methoxy, triflyl, mesyl, tosyl, hydrogen, $C_1$–$C_4$ alkyl, $C_1$–$C_4$ alkenyl.

* * * * *